(12) United States Patent
Wada

(10) Patent No.: US 8,378,303 B2
(45) Date of Patent: Feb. 19, 2013

(54) INFRARED SPECTROPHOTOMETER AND AUXILIARY DEVICE THEREFOR

(75) Inventor: Kiyoshi Wada, Uji (JP)

(73) Assignee: Shimadzu Corporation, Kyoto (JP)

( * ) Notice: Subject to any disclaimer, the term of this patent is extended or adjusted under 35 U.S.C. 154(b) by 341 days.

(21) Appl. No.: 12/631,610

(22) Filed: Dec. 4, 2009

(65) Prior Publication Data

US 2010/0243902 A1 Sep. 30, 2010

(30) Foreign Application Priority Data

Mar. 26, 2009 (JP) ................................. 2009-076168

(51) Int. Cl.
*G01J 5/02* (2006.01)
(52) U.S. Cl. ................................ 250/339.08
(58) Field of Classification Search ............. 250/339.08, 250/339.11, 339.1, 339.07
See application file for complete search history.

(56) References Cited

U.S. PATENT DOCUMENTS

| 6,002,133 A | 12/1999 | Nelson et al. | |
|---|---|---|---|
| 7,255,835 B2 * | 8/2007 | Franzen et al. | ............ 422/82.11 |
| 2004/0056198 A1 | 3/2004 | Tanaka | |
| 2007/0125950 A1 | 6/2007 | Wang et al. | |

FOREIGN PATENT DOCUMENTS

| JP | 61-252504 A | 11/1986 |
|---|---|---|
| JP | 01-321339 A | 6/1988 |
| JP | 2002-071460 A | 3/2002 |
| JP | 2004-108970 A | 4/2004 |
| JP | 2008-275650 A | 11/2008 |

OTHER PUBLICATIONS

Extended European Search Report dated Feb. 21, 2011.

* cited by examiner

*Primary Examiner* — David Porta
*Assistant Examiner* — Faye Boosalis
(74) *Attorney, Agent, or Firm* — Sughrue Mion, PLLC

(57) ABSTRACT

An infrared spectrophotometer, which is capable of preventing measurement data measured from being adversely affected by moisture vapor. An internal space of an attachment receiving therein an optical element is sealed and isolated from ambient air by providing a tube and others, and a dehumidifier is provided in the internal space of the attachment for an optical path. Thus, the dehumidifier is disposed in a relatively narrow space, so that the internal space of the attachment can be efficiently dehumidified within a short period of time so as to reduce humidity in the internal space to suppress absorption of moisture vapor which would otherwise occur on the optical path in the internal space of the attachment. This makes it possible to prevent a negative influence of moisture vapor on measurement data, while reducing a standby time due to the dehumidification.

24 Claims, 3 Drawing Sheets

INFRARED SPECTROPHOTOMETER AND AUXILIARY DEVICE THEREFOR

BACKGROUND OF THE INVENTION

1. Field of the Invention

The present invention relates to an infrared spectrophotometer for measuring infrared absorption spectra of a sample to analyze substances in the sample qualitatively and quantitatively, and an attachment for use with the infrared spectrophotometer.

2. Description of the Background Art

An infrared spectrophotometer is designed to measure a spectrum of light transmitted through a target sample while irradiating the sample with infrared light, and determine a wavelength of light absorbed in or transmitted through the sample to analyze components of the sample.

A Fourier-transform infrared (hereinafter also referred to as "FTIR") spectrophotometer is equipped with an interferometer in order to produce infrared coherent light. In the interferometer, an optical element, such as a beam splitter, is made of a material having deliquescent properties (properties of melting by absorbing moisture in air), such as potassium bromide (KBr). If deliquescence of the optical element occurs, it will preclude satisfactory measurements. Therefore, in order to prevent the deliquescence of the optical element, measures have been taken, for example, by placing the optical element in an element-receiving space, such as a low-humidity space gastightly isolated from ambient air while minimizing moisture vapor therein, or a vacuum space kept in a vacuumed state (see, for example, JP 2004-108970A and JU 3116465B).

During an infrared spectrophotometric measurement, if moisture vapor exists in any optical path, it will exert a negative effect on a measurement result, for example, an absorption peak of the moisture vapor will appear on measurement data, because moisture vapor has absorption peaks in a wavelength band of target substances. Thus, there is a need for additionally eliminating moisture vapor from an optical path in a device other than the interferometer, such as a sample chamber, by replacing internal air of the device with external dry air or nitrogen (performing an air-purging operation), on a case-by-case basis.

The infrared spectrophotometer is capable of measuring infrared absorption spectra of various types of gas, liquid and solid samples. The infrared spectrophotometric measurement is performed by an appropriate method selected depending on a type of sample, an intended purpose of measurement, etc. For example, the infrared spectrophotometric measurement method includes a transmission method, a reflection method, an ATR method, and various other methods.

For example, the reflection method can be used in a measurement for a substance absorbed in or applied to a material non-transmissive to infrared light, such as a metal plate. A reflection measurement for determining a reflectivity of a substance includes a method (regular reflection method or specular reflection method) in which infrared light is emitted to an entrance surface at an angle approximately perpendicular thereto, and a method (called "high-sensitivity reflection method" or "RAS (Reflection Absorption Spectrometry) method") in which infrared light is emitted to an incidence surface at an angle approximately parallel thereto to measure a thin sample layer (thin film) on a substrate.

The ATR method can be used in obtaining absorption spectra of a smooth planar surface of a solid sample, a powder sample, or a liquid sample. ATR stands for Attenuated Total Reflection. In the ATR method, light totally reflected by a surface of a sample can be measured to obtain an absorption spectrum of the sample surface.

In the infrared spectrophotometric measurements, a plurality of types of attachments each having at least one optical element of an optical system suitable for a specific one of the various measurement method, such as an attachment for the regular reflection method (regular reflection attachment) and an attachment for the ATR method (ATR attachment), are prepared, and a measurer or operator performs the measurements while replacing between the attachments depending on an intended one of the measurement methods to form an optical system corresponding to the intended measurement method, in many cases.

An internal space of the interferometer is dehumidified so as to keep humidity at a low level in consideration of influences primarily on an optical element. However, the interferometer is designed with little regard for influences of moisture vapor on measurement data. Particularly, for example, during an operation of opening and closing a sample chamber, or an operation of replacing an attachment in the sample chamber with another one, any sections other than the interferometer, such as the sample chamber, and a pre-chamber and a detector chamber each in communication with the sample chamber, are opened to ambient air, so that moisture vapor in resulting incoming ambient air will intrude into an optical path.

Moisture (moisture vapor) not only damages the optical element but also adversely affects on infrared spectrum data. Moisture vapor has a wide absorption band, primarily, around 4000 to 3400 $cm^{-1}$, 2000 to 1300 $cm^{-1}$ and 400 $cm^{-1}$ in a mid-infrared region. Thus, an influence of moisture vapor appears on measurement data, which is likely to cause noises in the absorption wavelength band of moisture vapor, and an undesirable situation where peaks other than those of a target sample are observed in the measurement data.

In particular, under conditions that a large amount of moisture vapor is contained in ambient air, energy in the absorption wavelength band of moisture vapor becomes smaller, and thereby the measurement data is more likely to receive a negative influence and have noises.

Further, during an operation of changing a measurement sample, it is also necessary to open and close the sample chamber and, in some cases, replace the attachment with another one depending on the measurement sample. Consequently, internal air of the sample chamber and air surrounding the attachment disposed in the sample chamber are replaced with ambient air to cause intrusion of moisture vapor into an optical path.

SUMMARY OF THE INVENTION

In view of the above problems, it is an object of the present invention to provide an infrared spectrophotometer, particularly an FTIR spectrophotometer, which is less susceptible to an influence of moisture vapor, and an attachment therefor.

In order to achieve the above object, according to one aspect of the present invention, there is provided an infrared spectrophotometer comprising an attachment equipped with at least one optical element of an optical system thereof, wherein the optical element of the attachment is disposed in a casing, and a dehumidifier is provided inside the casing.

In one aspect of the present invention, an internal space of the auxiliary device for an optical pass is sealed by the casing, to prevent mixing of ambient air, and moisture in the internal space of the auxiliary device is eliminated by the dehumidifier. In addition, the internal space is relatively narrow, so that the dehumidifier can more quickly provide a lower-humidity internal atmosphere with high efficiency.

As above, the present invention makes it possible to suppress a negative influence of moisture vapor absorption on measurement data. Specifically, the internal space of the attachment can be directly dehumidified to more quickly provide a lower-humidity internal atmosphere. In addition, the internal space of the attachment is sealed to prevent mixing of humid ambient air, so that an amount of moisture in the internal atmosphere is more reliably kept at a low level.

DESCRIPTION OF THE EXEMPLARY EMBODIMENTS

Figure 1:
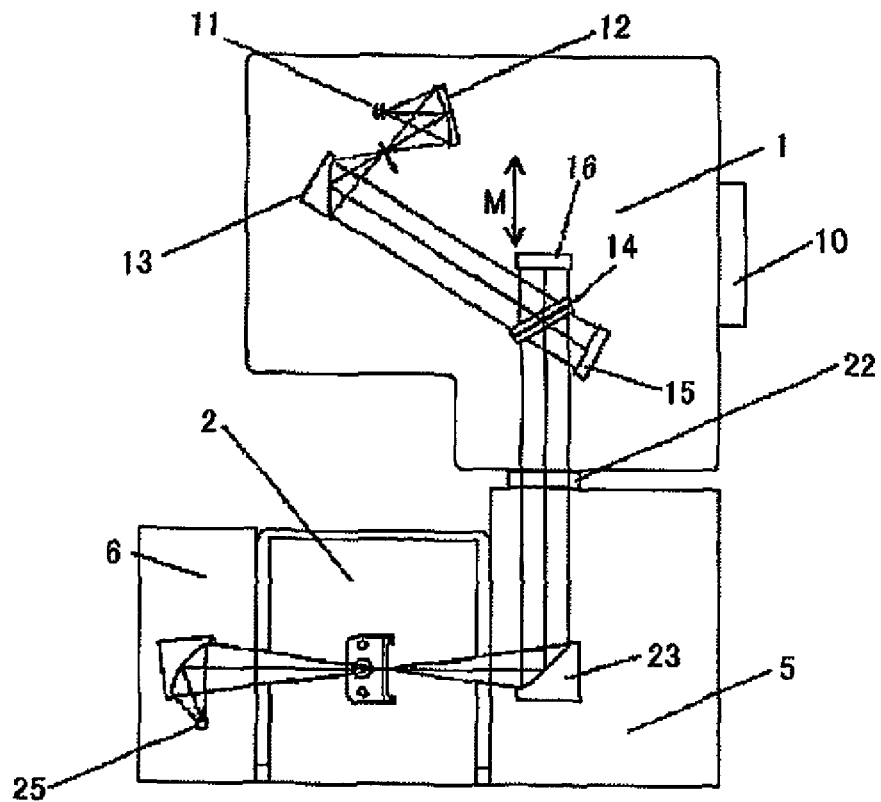
FIG. 1 is a schematic diagram showing an FTIR spectrophotometer in an FTIR spectrophotometer according to one embodiment of the present invention.

With reference to the drawings, the present invention will be described based on an embodiment thereof. FIG. 1 is a schematic diagram showing an FTIR (Fourier-transform infrared) spectrophotometer according to one exemplary embodiment of the present invention.

In FIG. 1, an interferometer 1 comprises an infrared light source 11, a collection mirror 12, a collimator mirror 13, a beam splitter 14, a stationary mirror 15 and a movable mirror 16. The interferometer 1 is operable to generate coherent infrared light for performing a spectrum measurement. Specifically, infrared light emitted from the infrared light source 11 enters a beam splitter 14 via the collection minor 12 and the collimator mirror 13. Through the beam splitter 14, the infrared light is split into two directions. The split infrared lights reflected by respective ones of the stationary mirror 15 and the movable mirror 16 are re-combined together, and then sent to an optical path directed to a sample chamber 2. During this process, the movable mirror 16 is reciprocatingly moved back and forth (in the arrowed direction M in FIG. 1), so that the combined light is formed as a coherent light (interferogram) having a time-varying amplitude. The coherent light output from the interferometer 1 through a window plate 22 is converged toward the sample chamber 2 by a collection mirror 23 located in a pre-chamber 5, and, after passing through a sample set in the sample chamber 2, converged toward an infrared photodetector 25 in a detector chamber 6. A received-light signal obtained by the infrared photodetector 25 is subjected to a data processing to create a spectrum.

The light source 11 and the beam splitter 14 constituting the interferometer are disposed inside the sealed interferometer 1 so as to be isolated from ambient air. The beam splitter 14 is generally made of a deliquescent material (such as KBr). Thus, a dehumidification element 10 is provided in a part of a wall of the interferometer 1.

In advance of an infrared spectrophotometric measurement, an attachment suitable for a measurement target is installed in the sample chamber 2. The attachment can be used by appropriately selecting one of a plurality of types of attachments each suitable for a plurality of measurement methods for use in infrared spectrophotometric measurements. For example, the attachment includes an ATR (attenuated total reflection) attachment, and a reflection attachment (regular-reflection attachment, a high-sensitivity-reflection attachment, etc.).

Figure 2:
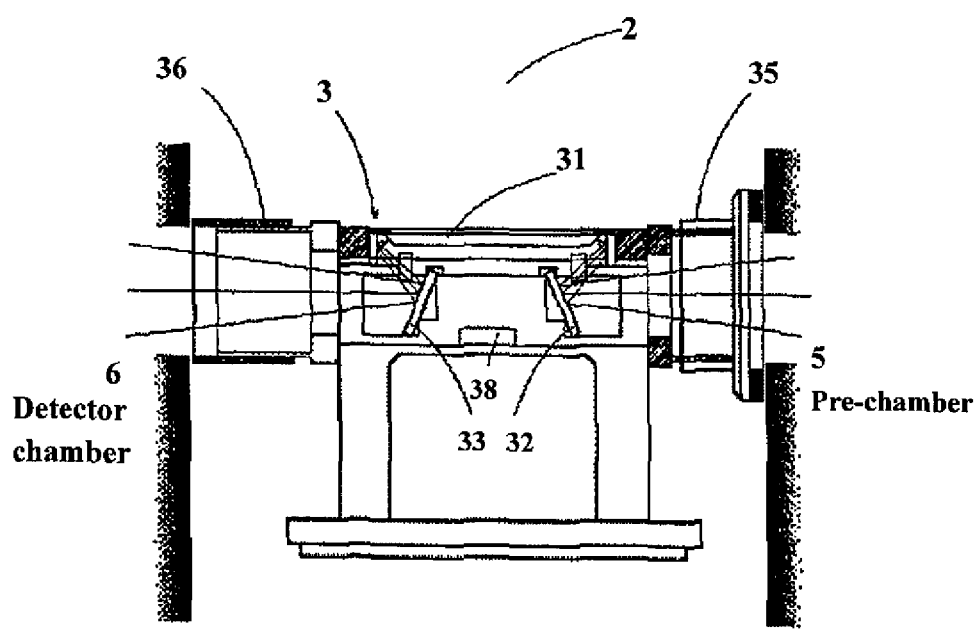
FIG. 2 is a schematic diagram showing an ATR attachment in the FTIR spectrophotometer according to the exemplary embodiment of the present invention.

FIG. 2 shows an ATR attachment 3 according to the exemplary embodiment of the present invention which is installed in the sample chamber 2. The attachment is equipped with an optical element, such as two mirrors 32, 33. The optical element of the attachment forms a part of the entire optical system for measurement light in the spectrophotometer. The ATR attachment is provided with a prism 31 in an upper wall thereof. A measurement sample can be brought into contact with the prism to measure an infrared absorption spectrum of a surface of the sample in contact with the prism. Infrared light from the interferometer is emitted on the mirror 32 disposed just below the prism, and led to one cross-sectional surface of the prism. Then, the infrared light receives an influence of infrared absorption of the sample while repeatedly undergoing total reflection inside the prism. The infrared light output from an opposite cross-sectional surface of the prism is directed to the detector via the mirror 33, and detected.

Respective internal spaces of the pre-chamber 5, the sample chamber 2, the sample chamber 2 and the detector chamber 6 are separated from each other by two partition walls provided between the pre-chamber 5 and the sample chamber 2 and between the sample chamber 2 and the detector chamber 6 and each formed with an opening for allowing measurement infrared light to pass therethrough. An internal space of the ATR attachment for allowing the light to pass therethrough is surrounded by the prism 31 and a casing including two tubes 35, 36, to isolate the internal of the ATR attachment for allowing the light to pass therethrough, from a remaining internal space of the sample chamber other than the ATR attachment. Each of the tubes 35, 36 has a double structure consisting of an inner tube and an outer tube. The outer tube is disposed to extend toward each of the partition walls and brought into contact with each of the partition walls, so that the respective internal spaces of the pre-chamber 5, the attachment and the detector chamber 6 are formed as a series of sealed spaces. A dehumidifier 38 is provided inside the casing at a position just below the prism, so that the sealed internal spaces are constantly dehumidified.

Figure 3:
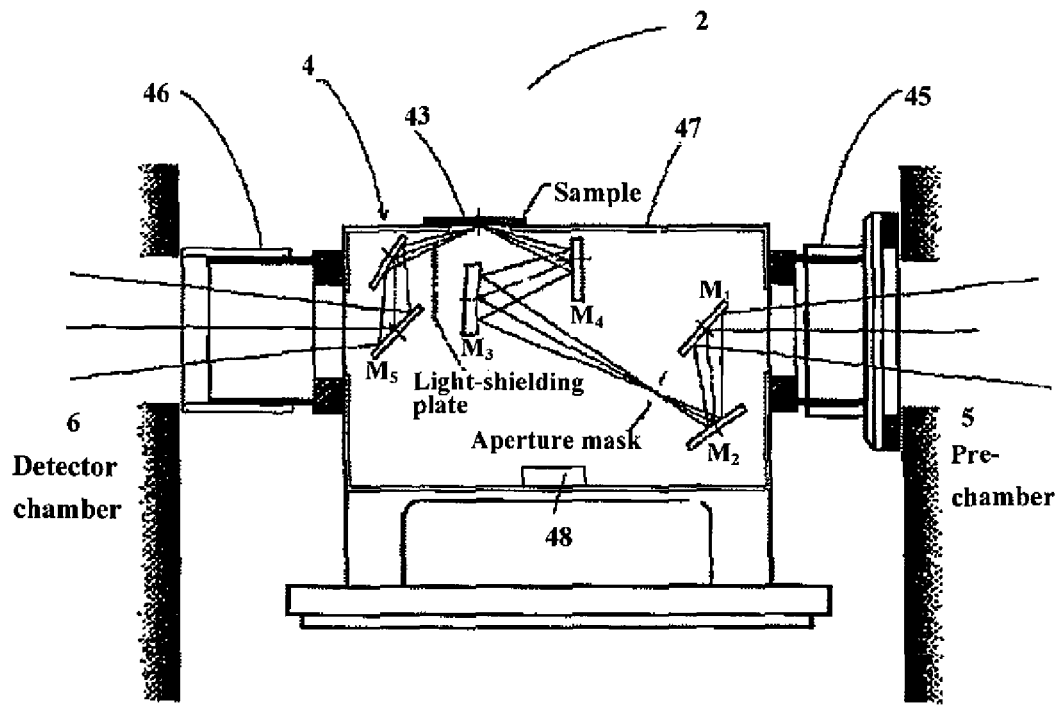
FIG. 3 is a schematic diagram showing a high-sensitivity-reflection attachment in an FTIR spectrophotometer according to another embodiment of the present invention.

The above embodiment has been described based on one example where the ATR attachment is used. Alternatively, any other type of attachment, such as a regular-reflection attachment or a high-sensitivity-reflection attachment, may be used to obtain the same advantageous effects as those in the FTIR spectrophotometer using the ATR attachment. For example, in a high-sensitivity-reflection attachment 4 as shown in FIG. 3, two tubes 45, 46 and a casing 47 may be arranged to allow an optical path to pass through a sealed space, and a dehumidifier 48 may be provided on a bottom of the casing. In the attachment for the reflection method (regular reflection method or high-sensitivity reflection method), an opening 43 is formed in the casing at a position corresponding to a sample setting position. The opening is closed when a measurement sample is set at a measurement position, so that the casing can be sealed to form a sealed space therein. In the reflection attachment, although the sealing is broken during each change of a sample, the present invention can reduce a time period from a change of a sample through until an effect of dehumidification is exhibited to allow the measurement to be initiated, so that a standby time in a measurement for a large number of samples is reduced to shorten a time period required for an analysis. The attachment 4 is equipped with an optical element, such as five mirrors $M_1$-$M_5$.

Generally, in a high-sensitivity reflection measurement, it is necessary to observe an extremely small peak (several mAbs in absorbance), and thereby a peak to be measured is likely to become indistinguishable due to an influence of moisture vapor. In a conventional infrared spectrophotometer, it is impossible to perform a sufficient measurement for a sample having extremely weak absorption in the absorption band of moisture band. The present invention makes it possible to perform a sufficient measurement for such a sample.

Each of the dehumidifiers 38, 48 may be comprised of a dehumidification agent, such as silica gel, CaO or molecular sieve, or may be comprised of an electric dehumidification drier, such as a Peltier device or an electrolytic device. The electric dehumidification drier has a capability to provide a high dehumidification effect at a high speed, although it requires a power supply. Thus, the measurement can be performed in a low-humidity atmosphere. In addition, even if the internal atmosphere is replaced with ambient air due to an operation of opening the sample chamber, the resulting humid atmosphere can be returned to a low-humidity state within a short period of time to reduce a time between sample measurements.

In the case where the electric dehumidification drier is used as the dehumidifier, a connector for supplying electric power may be provided in the sample chamber 2 of the infrared spectrophotometer to allow electric power to be supplied from the infrared spectrophotometer to the electric dehumidification drier. This eliminates a need for providing an additional power supply to the electric dehumidification drier.

In the case where the Peltier device is used as the electric dehumidification drier, a cold side of the Peltier device is disposed in the sealed chamber, and a water absorbent material is provided to extend from the cold side to an outside of the sealed chamber. Specifically, moisture vapor cooled by the Peltier device is condensed into water. Then, the water is transferred to the outside through the absorbent material, so that it is re-vaporized outside the sealed chamber, and released to ambient air.

The electrolytic device comprises a proton conductive solid electrolyte, and two porous electrodes sandwiching the proton conductive solid electrolyte therebetween. In the case where the electrolytic device is used as the electric dehumidification drier, when a current is supplied to the porous electrodes, moisture in the sealed chamber passes through the electrolytic device as protons, and moves toward the outside of the sealed chamber. During this process, respective outside and inside of the sealed chamber are separated by the electrolytic device. Thus, the water can be released to the outside, while keeping the sealed chamber in a sealed state.

Figure 4:
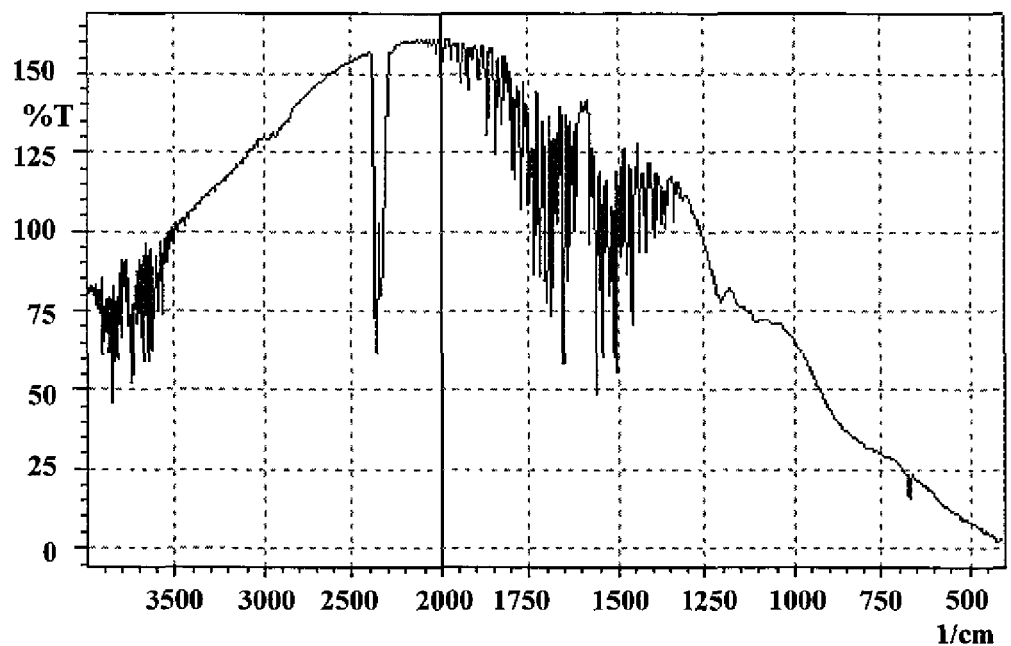
FIG. 4 is a graph (power spectrum) showing an influence of moisture vapor in a conventional FTIR spectrophotometer.
Figure 5:
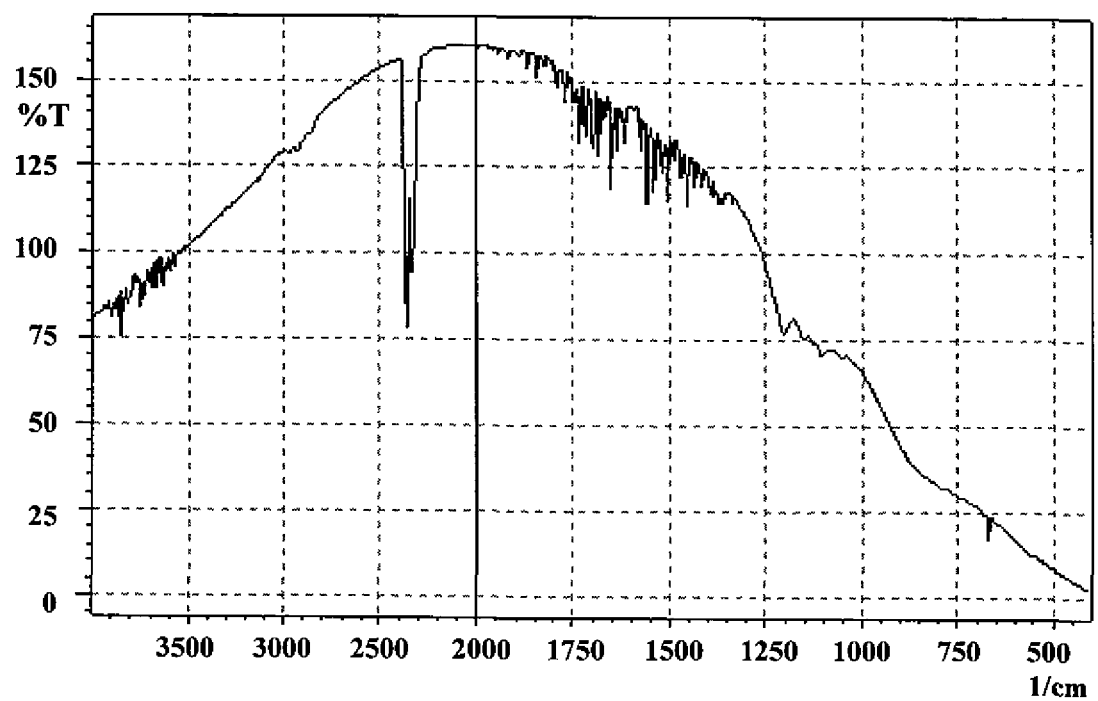
FIG. 5 is a graph (power spectrum) showing an influence of moisture vapor in an FTIR spectrophotometer of the present invention.

FIG. 4 shows a power spectrum obtained by a conventional FTIR spectrophotometer, and FIG. 5 shows a power spectrum obtained by an FTIR spectrophotometer in accordance with an exemplary embodiment of the present invention. In FIG. 4, sharp absorption peaks of moisture vapor largely appear around 4000 to 3400 cm$^{-1}$ and 2000 to 1300 cm$^{-1}$, and energy in the absorption wavelength band of moisture vapor is reduced to about one-half of energy from an original light source. In contrast, in FIG. 5, based on dehumidification of the internal space of the attachment for an optical path, according to the present invention, absorption of moisture vapor is significantly reduced, and a negative influence on the measured spectrum is significantly suppressed.

As mentioned above, in the infrared spectrophotometer of the exemplary embodiment of the present invention, a dehumidifier is provided in the internal space of the attachment for an optical path, so that, a space to be adversely affected by moisture is relatively small, as compared to case where the dehumidifier is provided in the sample chamber. Thus, the internal space of the attachment can be efficiently dehumidified within a short period of time.

What is claimed is:

1. An attachment, comprising:
a casing;
a dehumidifier; and
at least one optical element of an optical system of an infrared spectrophotometric analyzer, wherein
the optical element and the dehumidifier are disposed inside the casing and the casing is adapted to be detachably attached to a body of the analyzer.

2. The attachment as defined in claim 1, wherein the dehumidifier is an electric dehumidification unit.

3. The attachment as defined in claim 1, wherein, the optical element is an attenuated total reflection attachment.

4. The attachment as defined in claim 3, wherein a sample can be brought into a contact with a prism to measure an infrared absorption spectrum of a surface of the sample in contact with the prism.

5. The attachment as defined in claim 1, wherein the optical element is a regular reflection attachment.

6. The attachment as defined in claim 1, wherein the optical element is high-sensitivity-reflection attachment.

7. The attachment as defined in claim 1, wherein a sample is disposed in the casing.

8. The attachment as defined in claim 1, wherein the attachment is a sample chamber located between a detector chamber and a pre-chamber.

9. The attachment as defined in claim 8, wherein, the sample chamber and the detector chamber are separated from each other by two partition walls provided between the sample chamber and the detector chamber and formed with an opening for allowing measurement infrared light to pass therethrough.

10. The attachment as defined in claim 8, wherein, the sample chamber and the pre-chamber are separated from each other by two partition walls provided between the sample chamber and the pre-chamber and formed with an opening for allowing measurement infrared light to pass therethrough.

11. The attachment as defined in claim 1, wherein an infrared light passes through the casing.

12. The attachment as defined in claim 1,
wherein the casing is configured to be attached to a pre-chamber on a first face of the casing and is configured to be attached to a detector chamber on a second face opposite of the first face of the casing.

13. An infrared spectrophotometer, comprising:
a detachable attachment wherein at least one optical element of an optical system thereof and a dehumidifier are provided inside the attachment.

14. The infrared spectrophotometer as defined in claim 13, wherein the dehumidifier is an electric dehumidification unit, and wherein the infrared spectrophotometer has a sample chamber provided with a connector for supplying electric power to the electric dehumidification unit.

15. The infrared spectrophotometer as defined in claim 13, wherein the optical element is an attenuated total reflection attachment.

16. The infrared spectrophotometer as defined in claim 15, wherein a sample can be brought into contact with a prism to measure an infrared absorption spectrum of a surface of the sample in contact with the prism.

17. The infrared spectrophotometer as defined in claim 13, wherein the optical element is a regular reflection attachment.

18. The infrared spectrophotometer as defined in claim 13, wherein the optical element is high-sensitivity-reflection attachment.

19. The infrared spectrophotometer as defined in claim 13, wherein a sample is disposed in the attachment.

20. The infrared spectrophotometer as defined in claim 13, wherein the attachment is a sample chamber located between a detector chamber and a pre-chamber.

21. The infrared spectrophotometer as defined in claim 20, wherein, the sample chamber and the detector chamber are separated from each other by two partition walls provided between the sample chamber and the detector chamber and formed with an opening for allowing measurement infrared light to pass therethrough.

22. The infrared spectrophotometer as defined in claim 20, wherein, the sample chamber and the pre-chamber are separated from each other by two partition walls provided between the sample chamber and the pre-chamber and formed with an opening for allowing measurement infrared light to pass therethrough.

23. The infrared spectrophotometer as defined in claim 13, wherein an infrared light passes through the casing.

24. The infrared spectrophotometer as defined in claim 13, wherein the attachment is configured to be attached to a pre-chamber on a first face of the attachment and is configured to be attached to a detector chamber on a second face opposite of the first face of the attachment.

* * * * *